US009814396B2

(12) United States Patent
Futatsuyama et al.

(10) Patent No.: US 9,814,396 B2
(45) Date of Patent: Nov. 14, 2017

(54) PULSE WAVE SIGNAL PROCESSOR

(71) Applicant: DENSO CORPORATION, Kariya, Aichi-pref. (JP)

(72) Inventors: Kouki Futatsuyama, Kariya (JP); Taiji Kawachi, Kariya (JP); Tsuyoshi Nakagawa, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/289,263

(22) Filed: Oct. 10, 2016

(65) Prior Publication Data

US 2017/0105634 A1   Apr. 20, 2017

(30) Foreign Application Priority Data

Oct. 20, 2015 (JP) ................. 2015-206557

(51) Int. Cl.
| | | |
|---|---|---|
| *A61B 5/024* | (2006.01) | |
| *A61B 5/02* | (2006.01) | |
| *A61B 5/0205* | (2006.01) | |
| *A61B 5/00* | (2006.01) | |
| *A61B 5/021* | (2006.01) | |

(52) U.S. Cl.
CPC .......... *A61B 5/02007* (2013.01); *A61B 5/024* (2013.01); *A61B 5/0205* (2013.01); *A61B 5/02416* (2013.01); *A61B 5/6824* (2013.01); *A61B 5/7239* (2013.01); *A61B 5/02108* (2013.01)

(58) Field of Classification Search
CPC . A61B 5/02007; A61B 5/024; A61B 5/02416; A61B 5/02108
See application file for complete search history.

(56) References Cited

U.S. PATENT DOCUMENTS

| | | | |
|---|---|---|---|
| 2003/0199774 A1* | 10/2003 | Ogura ................ | A61B 5/02007 600/490 |
| 2007/0016085 A1 | 1/2007 | Inukai et al. | |
| 2012/0078123 A1 | 3/2012 | Futatsuyama et al. | |

FOREIGN PATENT DOCUMENTS

| | | |
|---|---|---|
| JP | H07-83742 B2 | 9/1995 |
| JP | 3487829 B2 | 1/2004 |
| JP | 3965435 B2 | 8/2007 |

(Continued)

*Primary Examiner* — Tammie K Heller
(74) *Attorney, Agent, or Firm* — Harness, Dickey & Pierce, P.L.C.

(57) ABSTRACT

In a pulse wave signal processor, a first filter attenuates a frequency component in an acquired pulse wave signal or in a differentiated pulse wave signal, and the attenuated frequency component is more than or equal to a first frequency. A second filter attenuates a frequency component in the acquired pulse wave signal, and the attenuated frequency component is less than the first frequency and more than or equal to a second frequency. A characteristic-point extractor extracts a characteristic point that exists in each single pulse of the pulse wave signal filtered by the second filter, and a signal separator partitioning the pulse wave signal or the differentiated signal filtered by the first filter into sections such that each section includes one of the extracted characteristic points. The partitioned sections are overlapped such that the characteristic points are coincident with each other, and arithmetically averaged.

7 Claims, 9 Drawing Sheets

(56) References Cited

FOREIGN PATENT DOCUMENTS

| | | | |
|---|---|---|---|
| JP | 4128788 | B2 | 7/2008 |
| JP | 4211472 | B2 | 1/2009 |
| JP | 4855721 | B2 | 1/2012 |
| JP | 5234078 | B2 | 7/2013 |

* cited by examiner

PULSE WAVE SIGNAL PROCESSOR

CROSS REFERENCE TO RELATED APPLICATION

This application is based on and incorporates herein by reference Japanese Patent Application No. 2015-206557 filed on Oct. 20, 2015.

TECHNICAL FIELD

The present disclosure relates to a pulse wave signal processor.

BACKGROUND

Up to now, a technology for estimating stiffness of a blood vessel or a blood pressure from a pulse wave signal or an acceleration pulse wave signal that is obtained by differentiating the pulse wave signal has been known. In order to estimate the stiffness of the blood vessel and the blood pressure correctly, a noise contained in the pulse wave signal or in the acceleration pulse wave signal is necessary to be reduced. Patent Document 1 (JP 3965435 B2) has proposed a method for reducing the noise contained in the acceleration pulse wave signal. First, in this method, the acceleration pulse wave signal is partitioned into multiple sections corresponding to respective pulses of a pulse wave. Next, the multiple sections are arithmetically averaged such that base points of the respective sections become coincident with each other. Lastly, the stiffness of the blood vessel or the blood pressure is estimated from the arithmetically-averaged acceleration pulse wave signal.

In the method of Patent Document 1, a wave profile of the arithmetically averaged acceleration pulse wave signal may become broad. Thus, necessary information for the estimation of the stiffness of the blood vessel or the blood pressure may be lost. This may be because the arithmetical averaging has not been performed correctly since the base point in each section is incorrect.

SUMMARY

It is an object of the present disclosure to provide a pulse wave signal processor capable of obtaining a pulse wave signal including necessary information for estimating stiffness of a blood vessel or a blood pressure.

According to an aspect of the present disclosure, a pulse wave signal processor includes a signal acquirer acquiring a pulse wave signal, a first filter executing a processing to attenuate a frequency component in the pulse wave signal acquired by the signal acquirer or in a differentiated signal that is obtained by differentiating the pulse wave signal, the frequency component attenuated by the first filter being more than or equal to a first frequency, a second filter executing a processing to attenuate a frequency component in the pulse wave signal acquired by the signal acquirer, the frequency component attenuated by the second filter being less than the first frequency and more than or equal to a second frequency, a characteristic-point extractor extracting a characteristic point that exists in each single pulse of the pulse wave signal processed by the second filter, a signal separator partitioning the pulse wave signal processed by the first filter or the differentiated signal processed by the first filter into sections corresponding to respective pulses of the pulse wave signal such that each section includes one of the extracted characteristic points, and an averaging calculator overlapping the partitioned sections such that the characteristic points are coincident with each other and arithmetically averaging the overlapped sections.

Therefore, the pulse wave signal processor of the present disclosure is capable of obtaining a pulse wave signal containing necessary information for estimating, for example, the stiffness of the blood vessel or the blood pressure.

BRIEF DESCRIPTION OF THE DRAWINGS

The disclosure, together with additional objectives, features and advantages thereof, will be best understood from the following description, the appended claims and the accompanying drawings, in which:

DETAILED DESCRIPTION

Figure 1:
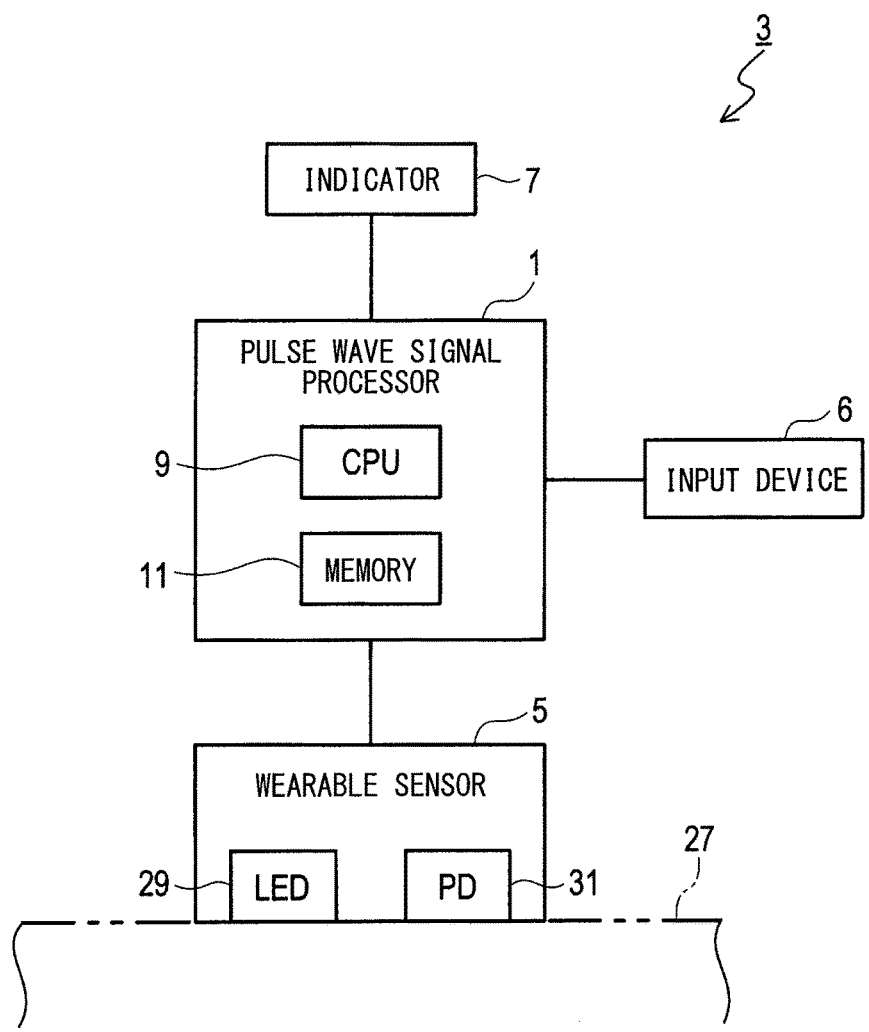
FIG. 1 is a block diagram illustrating a configuration of a pulse wave signal processing system according to an exemplar embodiment of the present disclosure.

An exemplar embodiment of the present disclosure will be described with reference to the drawings. A configuration of a pulse wave signal processor 1 and a configuration of a pulse wave signal processing system 3 including the pulse wave signal processor 1 will be described referring to FIGS. 1 and 2.

The pulse wave signal processing system 3 includes the pulse wave signal processor 1, a wearable sensor 5, an input device 6 and an indicator 7. The pulse wave signal processor 1 is constituted mainly by a known microcomputer which includes a CPU 9 and a memory 11 (e.g. semiconductor memory) such as RAM, ROM and a flash memory. A variety of functions of the pulse wave processor 1 are achieved by the CPU 9 executing programs stored in a non-transitory tangible storage medium.

In this case, the memory 11 is an example of the non-transitory tangible storage medium. The programs are executed, and methods corresponding to the programs are performed. The number of microcomputers included in the pulse wave signal processor 1 may be one or more than one.

Figure 2:
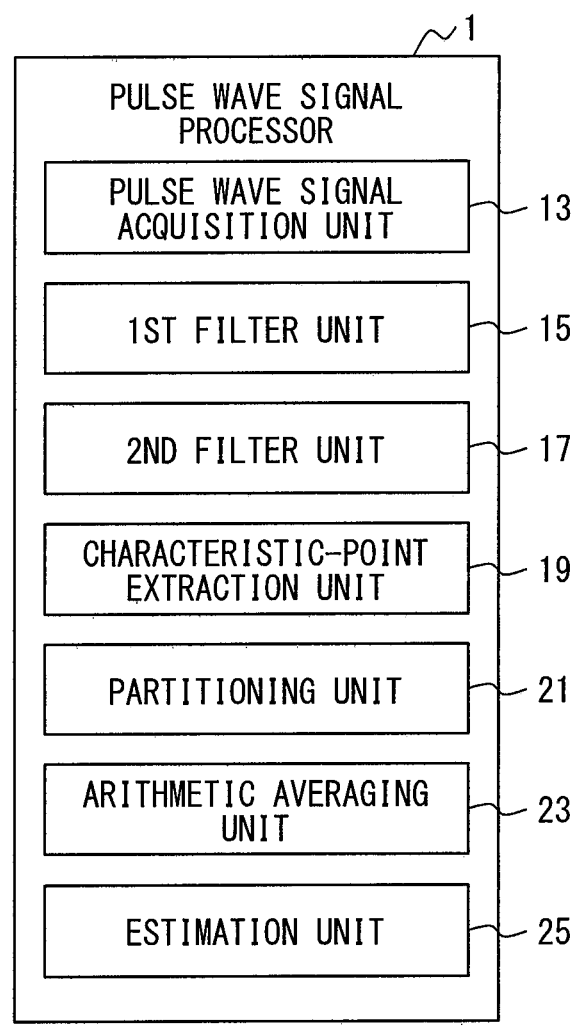
FIG. 2 is a block diagram illustrating a configuration of a pulse wave signal processor according to the embodiment.

The pulse wave signal processor 1 includes, as shown in FIG. 2, a pulse wave signal acquisition unit 13 (signal acquirer), a first filter unit 15 (first filter), a second filter unit 17 (second filter), a characteristic-point extraction unit 19 (characteristic-point extractor), a partitioning unit 21 (signal separator), an arithmetic averaging unit 23 (averaging calculator) and an estimation unit 25 (estimator), which are configurations of a function achieved by the CPU 9 through the execution of the programs.

The device for achieving these elements forming the pulse wave signal processor 1 is not limited. A part or all of the elements may be achieved by using a hardware including a logic circuit or an analog circuit, for example.

The wearable sensor 5 is attached to a wrist 27 of an examinee. The wearable sensor 5 includes an LED 29 and a PD (i.e. Photo Diode) 31. The LED 29 is a luminescence diode. The LED 29 irradiates a skin of the wrist 27 with green light. A wavelength of the green light is from 5000 Å to 8000 Å. The light is reflected in a capillary blood vessel. The PD 31 is a photo diode. The PD 31 receives the reflected light that has been reflected in the capillary blood vessel of the skin, and outputs an electric signal associated with the reflected light. The outputted electric signal is a pulse wave signal that varies in response to a pulse wave of the examinee. The wearable sensor 5 outputs the acquired pulse wave signal to the pulse wave signal processor 1.

The input device 6 is a switch that is to be operated by a user. When the input device 6 is operated by the user, the input device 6 outputs an operation signal to the pulse wave signal processor 1. The indicator 7 is, for example, a liquid crystal display capable of showing an image in accordance with a command from the pulse wave signal processor 1.

A pulse wave signal processing by the pulse wave signal processor 1 will be described with reference to FIGS. 3 to 17. The pulse wave signal processor 1 executes processes shown in FIG. 3 when the operation signal is inputted from the input device 6.

Figure 3:
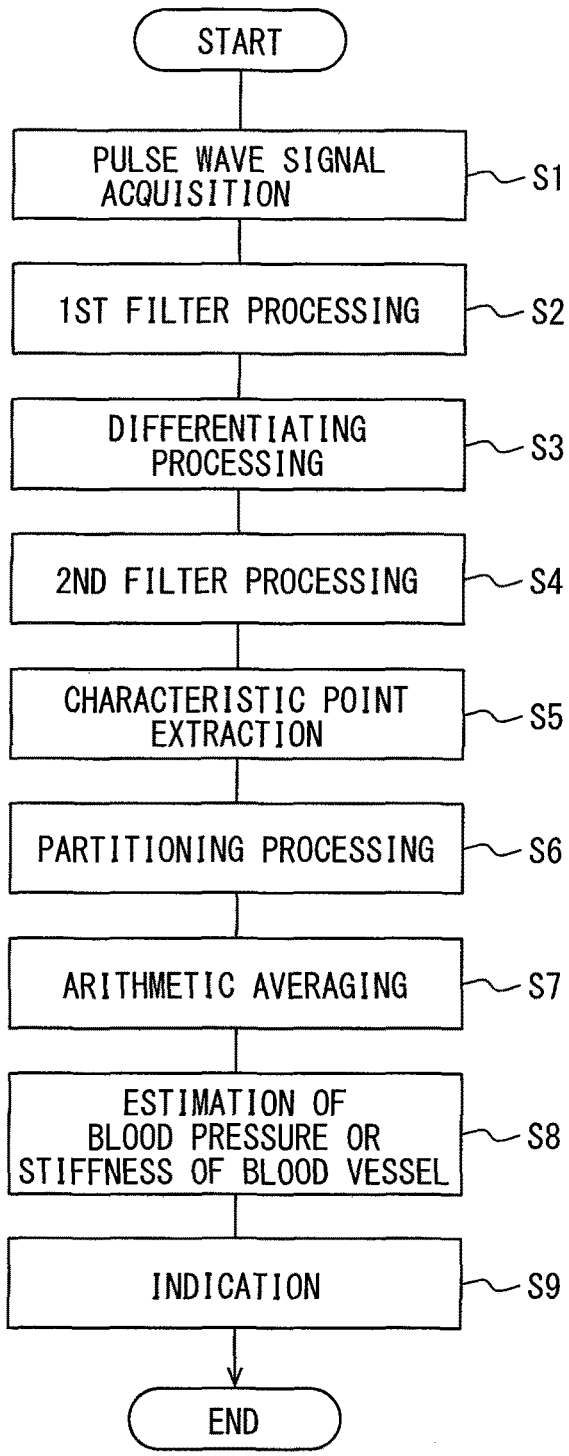
FIG. 3 is a flowchart illustrating processes executed by the pulse wave signal processor according to the embodiment.
Figure 4:
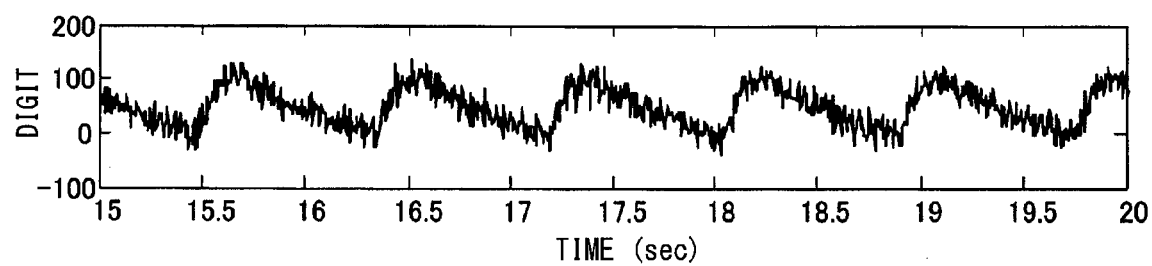
FIG. 4 is a diagram illustrating an example of a pulse wave signal.
Figure 5:
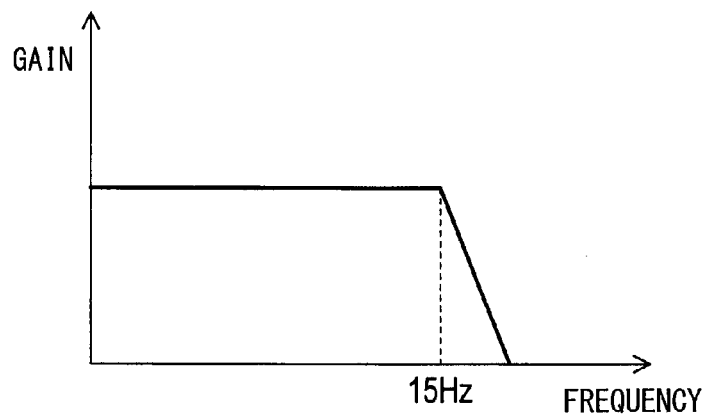
FIG. 5 is a diagram illustrating a frequency-gain characteristic of a low-pass filter used in a first filter processing, according to the embodiment.
Figure 6:
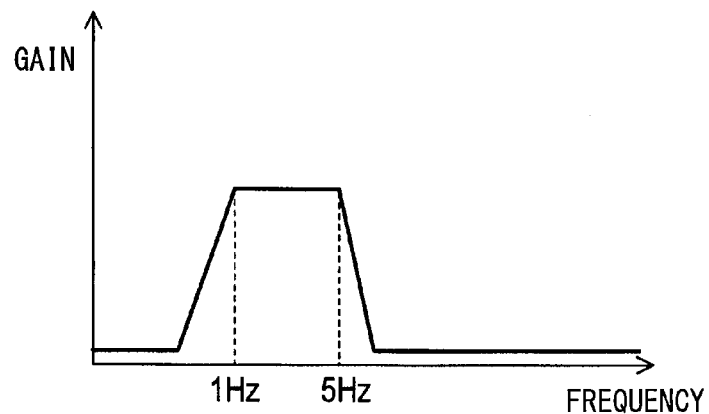
FIG. 6 is a diagram illustrating a frequency-gain characteristic of a high-pass filter used in a second filter processing, according to the embodiment.

At step S1 of FIG. 3, the pulse wave signal acquisition unit 13 acquires the pulse wave signal from the wrist 27 by using the wearable sensor 5. An example of the pulse wave signal is shown in FIG. 4. In the graph shown in FIG. 4, a horizontal axis represents time, and a vertical axis represents voltage of the pulse wave signal.

Figure 7:
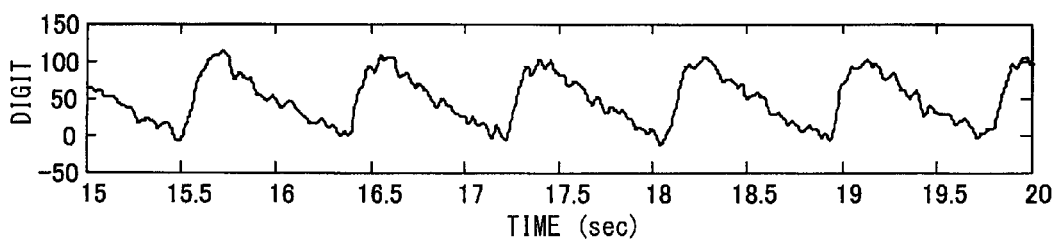
FIG. 7 is a diagram illustrating an example of a pulse wave signal after the first filter processing, according to the embodiment.

At step S2, the first filter unit 15 performs a first filter processing of the pulse wave signal acquired at step S1. In the first filter processing, a frequency component of the pulse wave signal higher than or equal to a first frequency is attenuated. More specifically, in the first filter processing, the pulse wave signal is filtered by using a low-pass filter that has a frequency-gain characteristic shown in FIG. 5. In the present embodiment, the first frequency is set at 15 Hz. Hereinafter, the pulse wave signal that has been subjected to the first filter processing is referred to as a first filtered pulse wave signal. An example of the first filtered pulse wave signal is shown in FIG. 7. The first frequency may be set arbitrarily within a range from 10 to 30 Hz, for example.

Figure 8:
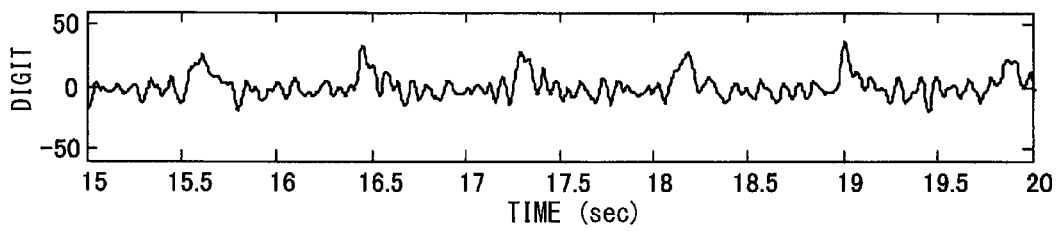
FIG. 8 is a diagram illustrating an example of a once differentiated signal, according to the embodiment.
Figure 9:
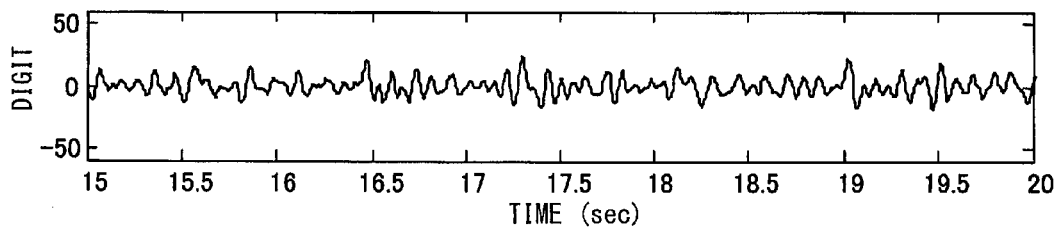
FIG. 9 is a diagram illustrating an example of a twice differentiated signal, according to the embodiment.
Figure 10:
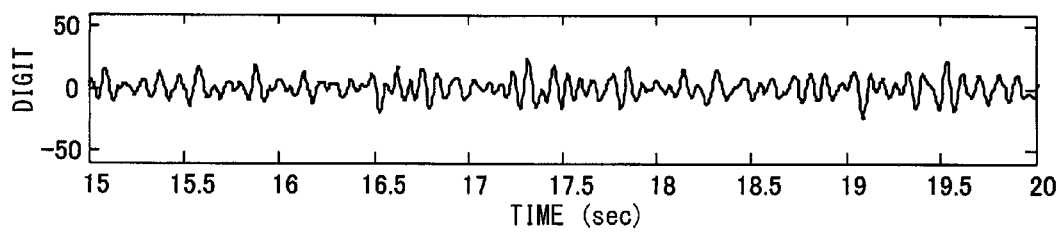
FIG. 10 is a diagram illustrating an example of a thrice differentiated signal, according to the embodiment.
Figure 11:
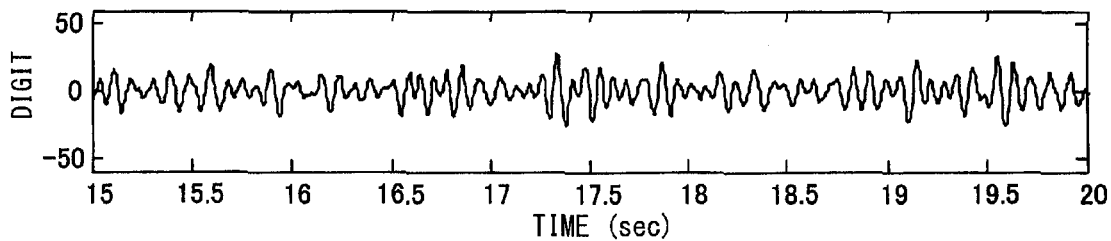
FIG. 11 is a diagram illustrating an example of a four times differentiated signal, according to the embodiment.

At step S3, the first filter unit 15 differentiates the first filtered pulse wave signal to obtain a once differentiated signal. The first filter unit 15 further differentiates the once differentiated signal to obtain a twice differentiated signal. Similarly, the first filter unit 15 further repeats the differentiating to obtain a thrice differentiated signal and a four times differentiated signal. FIG. 8 shows an example of the once differentiated signal, FIG. 9 shows an example of the twice differentiated signal, FIG. 10 shows an example of the thrice differentiated signal, and FIG. 11 shows an example of the four times differentiated signal. The once differentiated signal, the twice differentiated signal, the thrice differentiated signal and the four times differentiated signal may be referred to as a differentiated signal. The twice differentiated signal may be referred to as an acceleration pulse wave signal.

At step S4, the second filter unit 17 performs a second filter processing of the pulse wave signal acquired at step S1. In the second filter processing, a frequency component of the pulse wave signal higher than or equal to a second frequency is attenuated. More specifically, in the second filter processing, the pulse wave signal is filtered by using a low-pass filter that has a frequency-gain characteristic shown in FIG. 6.

Figure 12:
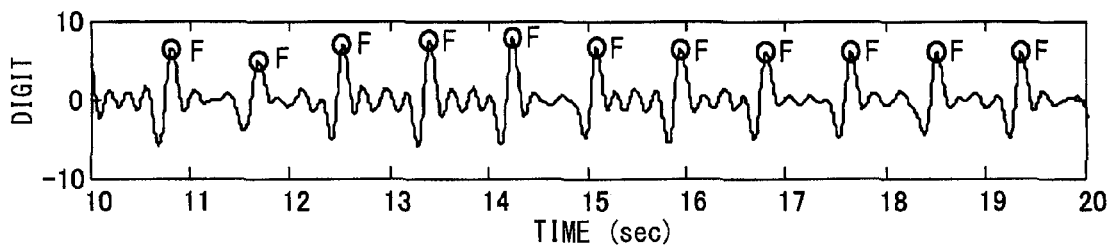
FIG. 12 is a diagram illustrating an example of a pulse wave signal after the second filter processing, according to the embodiment.

In the present embodiment, the second frequency is set at 5 Hz. The second frequency is lower than the first frequency. In the second filter processing, a frequency component lower than or equal to 1 Hz is also attenuated. Hereinafter, the pulse wave signal that has been subjected to the second filter processing is referred to as a second filtered pulse wave signal. An example of the second filtered pulse wave signal is shown in FIG. 12.

At step S5, the characteristic-point extraction unit 19 extracts characteristic points (i.e. characteristic time points) from the second filtered pulse wave signal. The extracted characteristic points exist in respective single pulses of the pulse wave. Each characteristic point is a point having a unique characteristic in a wave profile of the pulse wave signal or a point having a certain positional relationship with the point having the unique characteristic.

Each characteristic point is, more specifically, a point (referred to as a largest point, hereinafter) of the second filtered pulse wave at which a value of the second filtered pulse wave signal is largest in a single pulse of the pulse wave. The characteristic point may be a point (referred to as a smallest point, hereinafter) of the second filtered pulse wave at which the value of the second filtered pulse wave signal is smallest in a single pulse of the pulse wave. Alternatively, the characteristic point may be a midpoint between the largest point and the smallest point. FIG. 12 shows characteristic points F that are extracted as described above.

Figure 13:
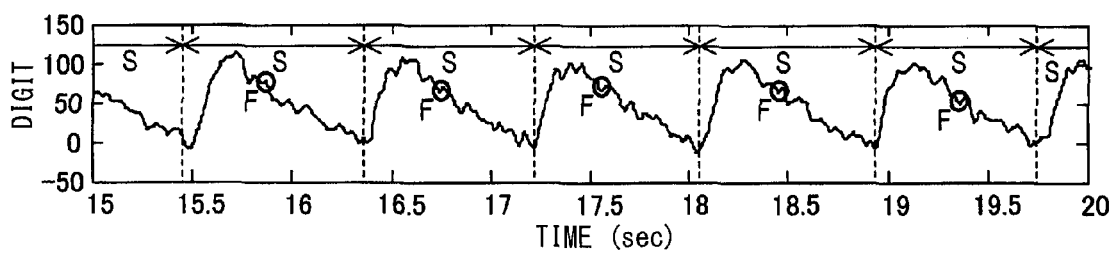
FIG. 13 is a diagram illustrating sections S and characteristic points F in the pulse wave signal after the first filter processing, according the embodiment.

At step S6, the partitioning unit 21 partitions the first filtered pulse wave signal into sections corresponding to the respective single pulses of the pulse wave. Each section has a length of one of the single pulses. When the first filtered pulse wave signal is partitioned into the sections, one of the characteristic points extracted at step S5 is included in each section. FIG. 13 shows multiple sections S generated by the partitioning and characteristic points F included in the respective sections S.

Figure 14:
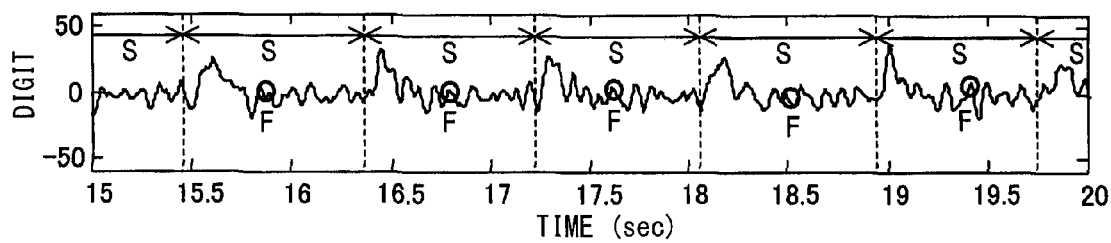
FIG. 14 is a diagram illustrating sections S and characteristic points F in the once differentiated signal, according to the embodiment.
Figure 15:
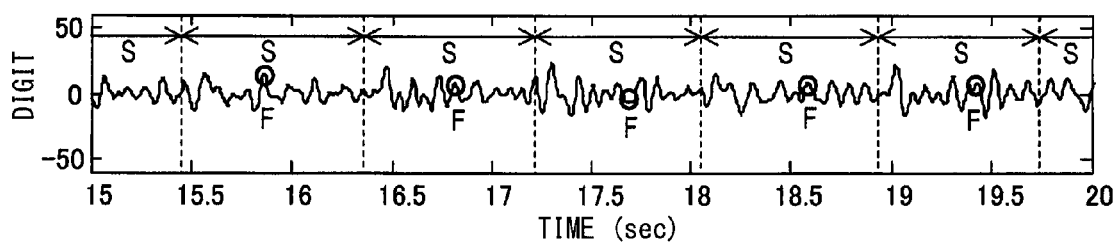
FIG. 15 is a diagram illustrating sections S and characteristic points F in the twice differentiated signal, according to the embodiment.
Figure 16:
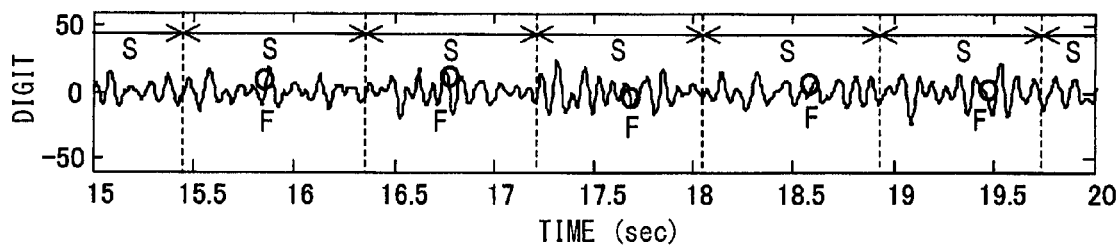
FIG. 16 is a diagram illustrating sections S and characteristic points F in the thrice differentiated signal, according to the embodiment.
Figure 17:
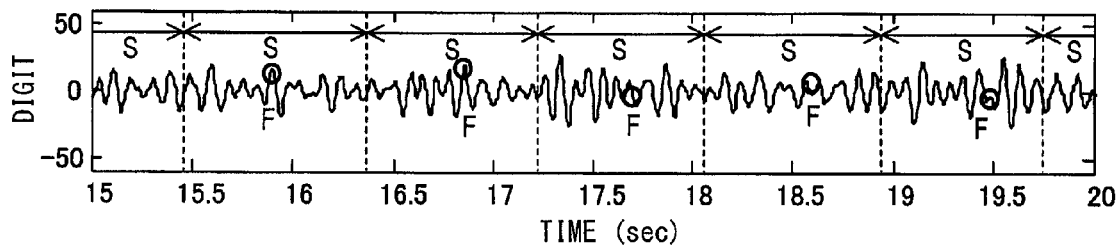
FIG. 17 is a diagram illustrating sections S and characteristic points F in the four times differentiated signal, according to the embodiment.

The partitioning unit 21 also partitions the once differentiated signal, the twice differentiated signal, the thrice differentiated signal and the four times differentiated signal, similarly. FIG. 14 shows multiple sections S generated by partitioning of the once differentiated signal and characteristic points F included in the respective sections S. FIG. 15 shows multiple sections S generated by partitioning of the twice differentiated signal and characteristic points F included in the respective sections S. FIG. 16 shows multiple sections S generated by partitioning of the thrice differentiated signal and characteristic points F included in the respective sections S. FIG. 17 shows multiple sections S generated by partitioning of the four times differentiated signal and characteristic points F included in the respective sections S.

At step S7, the arithmetic averaging unit 23 first corrects the first filtered pulse wave signal such that the lengths of the respective sections S become equal. The correction is performed by resampling. In other words, a part or all of the sections S are corrected to be enlarged or reduced with respect to the time axis. Then, the arithmetic averaging unit 23 arithmetically averages the corrected sections S. More specifically, the corrected sections S are arithmetically averaged such that the characteristic points F of the respective sections S are coincident with each other. In other words, the characteristic points F of the sections S are arithmetically averaged, and values at time points shifted by Δt from the characteristic points F in the sections S are arithmetically averaged. The Δt is a positive or negative arbitrary value and its unit is millisecond (msec). Hereinafter, the first filtered pulse wave signal that has been arithmetically averaged is referred to as an averaged pulse wave signal.

The arithmetic averaging unit 23 arithmetically averages also the once differentiated signal, the twice differentiated signal, the thrice differentiated signal and the four times differentiated signal, similarly. Hereinafter, the once differentiated signal that has been arithmetically averaged is referred to as an averaged once differentiated signal, the twice differentiated signal that has been arithmetically averaged is referred to as an averaged twice differentiated signal, the thrice differentiated signal that has been arithmetically averaged is referred to as an averaged thrice differentiated signal, and the four times differentiated signal that has been arithmetically averaged is referred to as an averaged four times differentiated signal.

At step S8, the estimation unit 25 performs a wave analysis on the averaged twice differentiated signal in a known method, thereby calculating a characteristic amount. A method of the wave analysis may employ a method described in Japanese Patent: JP 4128788 B2, for example.

Next, the estimation unit 25 uses the calculated characteristic amount to estimate stiffness of a blood vessel in a known method. A method of the estimation of the stiffness of the blood vessel may employ a method described in Japanese Patent: JP 3487829 B2. The estimation unit 25 uses the calculated characteristic amount to estimate a blood pressure. A method of the estimation of the blood pressure may employ a method described in Japanese Patent: JP 4855721 B2.

At step S9, the estimation unit 25 indicates the stiffness of the blood vessel and the blood pressure estimated at step S8 on the indicator 7.

Effects achieved by the pulse wave signal processor 1 will be described.

(1A) The pulse wave signal processor 1 extracts the characteristic points from the second filtered pulse wave signal. Therefore, the characteristic points can be extracted correctly.

(1B) The pulse wave signal processor 1 performs arithmetic averaging by using the correctly-extracted characteristic points, and thus the arithmetic averaging can be performed correctly. Accordingly, the averaged pulse wave signal, the averaged once differentiated signal, the averaged twice differentiated signal, the averaged thrice differentiated signal and the averaged four times differentiated signal become signals reflecting the characteristic points correctly. As a result, the stiffness of the blood vessel and the blood pressure can be estimated correctly from the signals that have been arithmetically averaged.

(1C) The first frequency is set more than or equal to 10 Hz. Therefore, it is highly effective for removal of noise contained in the pulse wave signal. Further, the stiffness of the blood vessel and the blood pressure can be measured more correctly.

(1D) The second frequency is set more than 1 Hz and less than 10 Hz. Therefore, the characteristic points can be extracted more correctly.

(1E) The pulse wave signal processor 1 acquires a pulse wave signal from the wrist 27. An S/N (i.e. signal-to-noise ratio) of the pulse wave signal acquired from the wrist 27 is generally small, but the stiffness of the blood vessel and the blood pressure can be correctly estimated from the pulse wave signal by using the pulse wave signal processor 1. The wearable sensor 5 is attachable to the wrist 27 and easy to be worn on the wrist 27. Accordingly, the stiffness of the blood vessel and the blood pressure can be measured on a daily basis.

(1F) The pulse wave signal processor 1 uses the largest points of the second filtered pulse wave signal as the characteristic points, at which a value of the second filtered pulse wave signal is largest in a single pulse of the pulse wave. The largest point is easy to be measured. Since the largest points are information related to pumping by a heart, an individual difference of the largest points are small. Therefore, it is more facilitated to extract the characteristic points correctly by using the largest points as the characteristic points.

Even when the smallest point of the second filtered pulse wave signal at which a value of the second filtered pulse wave signal is smallest in a single pulse of the pulse wave are used as the characteristic points, similar effects can be obtained. Alternatively, even when a point P which divides a time length between the largest point and the smallest point in a single pulse of the pulse wave at a predetermined ratio is used, similar effects can be obtained.

The above-described point P will be described below. The point P is positioned between the largest point and the smallest point on the time axis. A time difference between the largest point and the point P is defined as L1, and a time difference between the smallest point and the point P is defined as L2. A ratio between the L1 and L2 is the above-described predetermined ratio. The L1 and L2 are positive numbers. When the ratio between the L1 and L2 is 1:1, the point P is positioned at a midpoint between the largest point and the smallest point.

Tests for confirming the effects achieved by the pulse wave processor 1 will be described.

(1) Test 1

Figure 18:
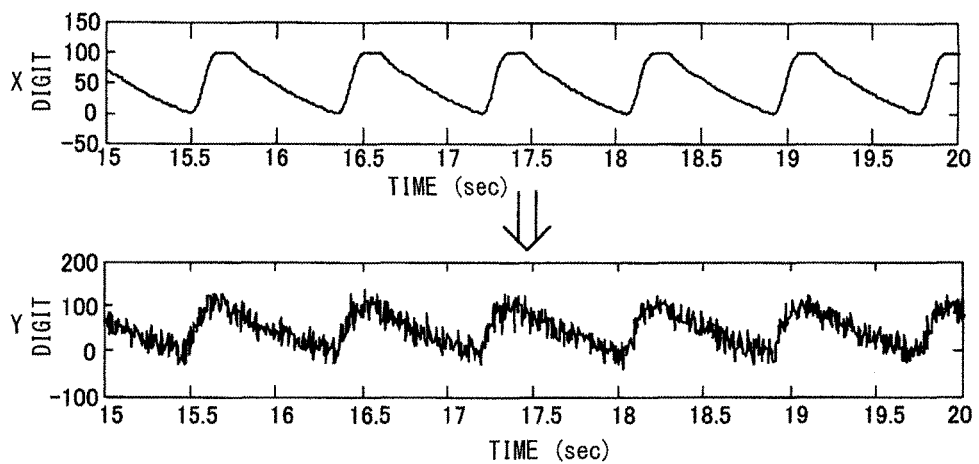
FIG. 18 is a diagram illustrating a simulation pulse wave signal X and a simulation pulse wave signal Y, according to the embodiment.

A simulation pulse wave signal X shown in FIG. 18 is produced. The simulation pulse wave signal X is artificially produced to have a regular-wave profile in imitation of an actual pulse wave signal. Pulse wave intervals of the simulation pulse wave signal X are set at approximately 1000 msec uniformly.

Next, a simulation pulse wave signal Y shown in FIG. 18 is produced by superimposing white noise on the simulation pulse wave signal X. The above-described pulse wave signal processing is performed on the simulation pulse wave signal Y. Further, a comparative processing, which is basically similar to but partially different from the above-described pulse wave signal processing, is performed on the simulation pulse wave signal Y. In the comparative processing, the characteristic points are not extracted from the second filtered pulse wave signal, but from the first filtered pulse wave signal.

Figure 19:
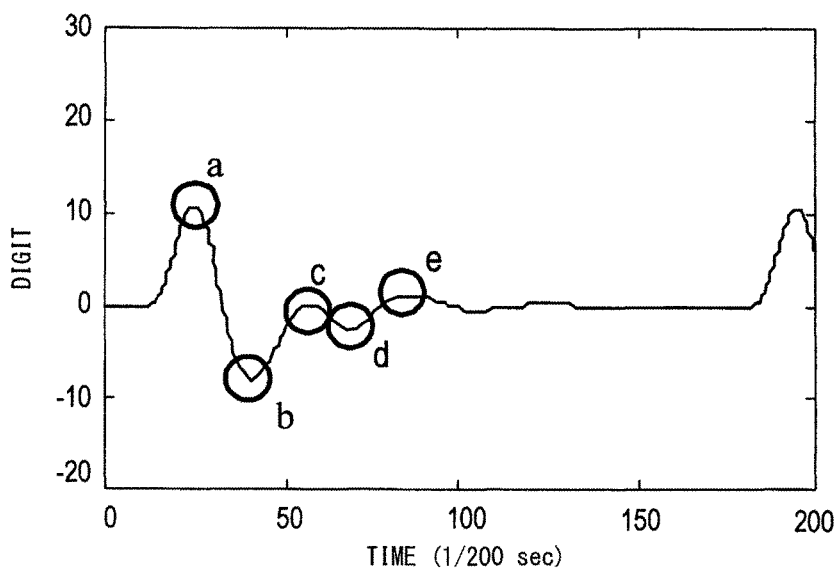
FIG. 19 is a diagram illustrating characteristic amounts a to e, according to the embodiment.

Next, the characteristic amounts a to e shown in FIG. 19 are calculated from the averaged twice differentiated signals obtained by the pulse wave signal processing. The characteristic amounts a to e are peak values of curves encircled in FIG. 19.

Similarly, the characteristic amounts a to e are calculated from the averaged twice differentiated signals obtained by the comparative processing. Furthermore, the characteristic amounts a to e are calculated from the twice differentiated signal of the simulation pulse wave signal X and from the twice differentiated signal of the simulation pulse wave signal Y. The characteristic amounts a to e calculated from the twice differentiated signal of the simulation pulse wave signal X on which noise is not superimposed are the most accurate.

Figure 20:
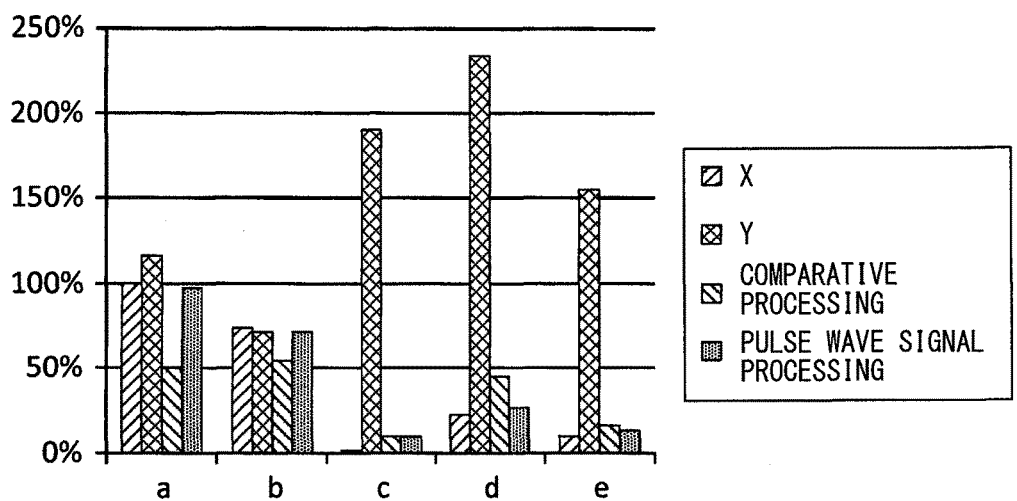
FIG. 20 is a diagram illustrating the characteristic values a to e calculated in respective conditions.

The calculated characteristic amounts a to e are shown in FIG. 20. The characteristic amount a calculated from the twice differentiated signal of the simulation pulse wave signal X is assumed to be 100%. "X" shown in FIG. 20 means the characteristic amounts calculated from the twice differentiated signal of the simulation pulse wave signal X, and "Y" shown in FIG. 20 means the characteristic amounts calculated from the twice differentiated signal of the simulation pulse wave signal Y. "PULSE WAVE SIGNAL PROCESSING" shown in FIG. 20 means the characteristic amounts calculated from the averaged twice differentiated signal that is obtained by performing the pulse wave signal processing of the simulation pulse wave signal Y. "COMPARATIVE PROCESSING" shown in FIG. 20 means the characteristic amounts calculated from the averaged twice differentiated signal that is obtained by performing the comparative processing with respect to the simulation pulse wave signal Y.

As shown in FIG. 20, the characteristic amounts a to e calculated from the averaged twice differentiated signal that is obtained by performing the pulse wave signal processing of the simulation pulse wave signal Y are near to the characteristic amounts a to e calculated from the twice differentiated signal of the simulation pulse wave signal X. In contrast, the characteristic amounts a to e calculated from the averaged twice differentiated signal that is obtained by performing the comparative processing of the simulation pulse wave signal Y are largely different from the characteristic amounts a to e calculated from the twice differentiated signal of the simulation pulse wave signal X.

According to the results, it can be confirmed that the characteristic amounts a to e can be calculated correctly by the pulse wave signal processing according to the present embodiment.

(2) Test 2

Similarly to the test 1, the simulation pulse wave signal Y is produced. With respect to the simulation pulse wave signal Y, processes of the pulse wave signal processing from start to the extraction of the characteristic points at step S5 of FIG. 3 are performed. Next, a time difference (referred to as a characteristic point interval) between two adjacent characteristic points is measured on 20 positions. Next, a standard deviation of the characteristic point intervals measured on the 20 positions is calculated.

The above-described process is repeatedly performed with changing the second frequency in a range from 2 to 50 Hz. The used second frequencies are 2, 2.5, 3, 4, 5, 6, 7.5, 10, 12.5, 15, 20, 30, 40 and 50 Hz. The results of the test are shown in FIG. 21.

When the white noise is removed, the simulation pulse wave signal Y has a regular-wave profile. Therefore, as the extracted characteristic points become more accurate, the characteristic point interval becomes more uniform, and the standard deviation of the characteristic point intervals becomes smaller.

Figure 21:
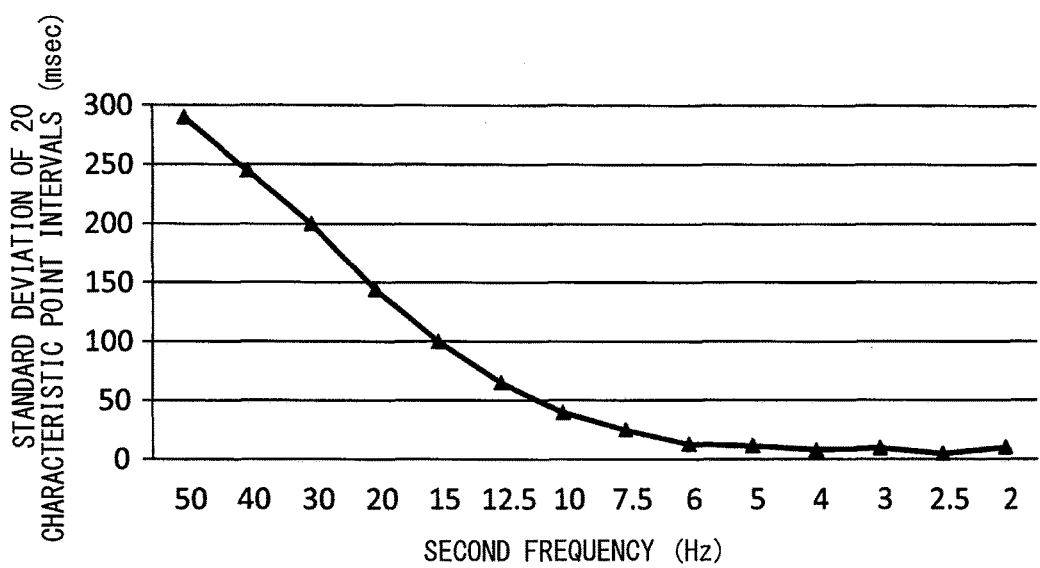
FIG. 21 is a diagram illustrating a relationship between a second frequency and a standard deviation of characteristic point intervals.

As shown in FIG. 21, as the second frequency becomes smaller, the standard deviation of the characteristic point intervals becomes smaller. Especially, when the second frequency is less than 10 Hz, the standard deviation of the characteristic point intervals is further small. Therefore, as the second frequency becomes smaller, the characteristic points can be extracted more correctly.

Although the present disclosure has been fully described in connection with the preferred embodiments thereof with reference to the accompanying drawings, it is to be noted that various changes and modifications described below will become apparent to those skilled in the art.

(1) The pulse wave signal processor 1 may include a sensor that has a similar configuration to the wearable sensor 5 and is attached to a housing of the pulse wave signal processor 1. The pulse wave signal processor 1 is capable of obtaining a pulse wave signal by using the sensor. The sensor is capable of obtaining a pulse wave signal from a part of the body of the examinee other than the wrist 27. For example, the part other than the wrist may be an end of a finger of the examinee. Generally, a flow rate of blood in the end of the finger is relatively low in a low temperature environment, and it is generally difficult to obtain an accurate pulse wave signal. However, a pulse wave signal containing necessary information for estimation of the stiffness of the blood vessel or the blood pressure can be obtained from the end of the finger by using the pulse wave signal processor 1 according to the present disclosure.

(2) The pulse wave signal processor 1 may include one or both of the indicator 7 and the input device 6.

(3) The pulse wave signal processor 1 may differentiate a pulse wave signal, and then may perform the first filter processing of the differentiated signal. Alternatively, the pulse wave signal processor 1 may perform the differentiating and the first filter processing of a pulse wave signal, simultaneously. In this case, a first filter having a function to perform the differentiating and a function to perform the first filter processing can be used.

(4) The pulse wave signal processor 1 may output one or more of the averaged pulse wave signal, the averaged once differentiated signal, the averaged twice differentiated signal, the averaged thrice differentiated signal and the averaged four times differentiated signal to an external device. The external device is capable of estimating the stiffness of the blood vessel and the blood pressure by using the outputted signals. In this case, the pulse wave signal processor 1 may not estimate the stiffness of the blood vessel or the blood pressure.

(5) The pulse wave signal processor 1 may estimate a state quantity other than the stiffness of the blood stiffness and the blood pressure by using one or more of the averaged pulse wave signal, the averaged once differentiated signal, the averaged twice differentiated signal, the averaged thrice differentiated signal and the averaged four times differentiated signal.

(6) The pulse wave signal processor 1 may estimate the stiffness of the blood vessel and the blood pressure by using one or more of the averaged pulse wave signal, the averaged once differentiated signal, the averaged thrice differentiated signal and the averaged four times differentiated signal.

(7) The pulse wave signal processor 1 may perform the first filter processor or the second filter processing by using an analog circuit.

(8) A function of a single component of the above-described embodiment may be distributed to multiple components. Functions of multiple components may be integrated into a single component. A part of the configuration of the above-described embodiment may be omitted.

(9) Other than the above-described pulse wave signal processor, the invention disclosed by the present disclosure can be achieved by a variety of configurations, for example, a system including the pulse wave signal processor as a component, a program causing a computer to function as the pulse wave signal processor, a non-transitory tangible storage medium such as a semi-conductor memory into which the program is stored, or a pulse wave signal processing method.

Additional advantages and modifications will readily occur to those skilled in the art. The disclosure in its broader terms is therefore not limited to the specific details, representative apparatus, and illustrative examples shown and described.

What is claimed is:

1. A pulse wave signal processor comprising:
   a signal acquirer configured to acquire a pulse wave signal;
   a first filter configured to attenuate a frequency component in the pulse wave signal acquired by the signal acquirer or in a differentiated signal that is obtained by differentiating the pulse wave signal, the frequency component attenuated by the first filter being more than or equal to a first frequency;
   a second filter configured to attenuate a frequency component in the pulse wave signal acquired by the signal acquirer, the frequency component attenuated by the second filter being less than the first frequency and more than or equal to a second frequency;
   a characteristic-point extractor configured to extract a characteristic point that exists in each single pulse of the pulse wave signal processed by the second filter;
   a signal separator configured to partition the pulse wave signal processed by the first filter or the differentiated signal processed by the first filter into sections corresponding to respective pulses of the pulse wave signal such that each section includes one of the extracted characteristic points; and
   an averaging calculator configured to overlap the partitioned sections such that the characteristic points are coincident with each other and arithmetically averaging the overlapped sections.

2. The pulse wave signal processor according to claim 1, wherein the first frequency is higher than or equal to 10 Hz.

3. The pulse wave signal processor according to claim 1, wherein the second frequency is higher than 1 Hz and lower than 10 Hz.

4. The pulse wave signal processor according to claim 1, wherein the signal acquirer is configured to acquire the pulse wave signal from a wrist of an examinee.

5. The pulse wave signal processor according to claim 1, wherein the differentiated signal is obtained by differentiating the pulse wave signal twice or four times.

6. The pulse wave signal processor according to claim 1, wherein the characteristic point is a largest point at which a value of the pulse wave signal is largest, a smallest point at which the value of the pulse wave signal is smallest, or a point which separates a distance between the largest point and the smallest point at a predetermined ratio.

7. The pulse wave signal processor according to claim 1, further comprising an estimator configured to estimate stiffness of a blood vessel or a blood pressure by using the pulse wave signal or the differentiated signal averaged by the averaging calculator.

* * * * *